US008485826B2

(12) United States Patent
Harada et al.

(10) Patent No.: US 8,485,826 B2
(45) Date of Patent: Jul. 16, 2013

(54) PORTABLE TERMINAL DEVICE HAVING FUNCTION OF MEASURING MENTAL FATIGUE AND ITS MEASURING METHOD

(75) Inventors: Nobuyoshi Harada, Ikeda (JP); Sunao Iwaki, Ikeda (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 975 days.

(21) Appl. No.: 12/558,894

(22) Filed: Sep. 14, 2009

(65) Prior Publication Data

US 2010/0041002 A1 Feb. 18, 2010

Related U.S. Application Data

(63) Continuation of application No. PCT/JP2008/053816, filed on Mar. 4, 2008.

(30) Foreign Application Priority Data

Mar. 13, 2007 (JP) .................................. 2007-063274

(51) Int. Cl.
*G09B 19/00* (2006.01)
(52) U.S. Cl.
USPC .......................................................... 434/236
(58) Field of Classification Search
USPC .......................................................... 434/236
See application file for complete search history.

(56) References Cited

U.S. PATENT DOCUMENTS 2,495,708 A * 1/1950 Draeger et al. ............... 351/243

FOREIGN PATENT DOCUMENTS

| JP | 2001-218756 A | 8/2001 |
|---|---|---|
| JP | 2001-309887 A | 11/2001 |
| JP | 2003-070773 A | 3/2003 |
| JP | 2004-174041 A | 6/2004 |

OTHER PUBLICATIONS

Hashimoto, Kunie; "Seishin Hiro no Kensa"; The Japanese Journal of Ergonomics, Jun. 15, 1981, vol. 17, No. 3, pp. 107-113 (partial translation).
International Search Report of PCT/JP2008/053816, Mailing Date of Apr. 1, 2008.

* cited by examiner

*Primary Examiner* — Robert J Utama
*Assistant Examiner* — Evan Page
(74) *Attorney, Agent, or Firm* — Westerman, Hattori, Daniels & Adrian, LLP

(57) ABSTRACT

A portable terminal device (1) capable of easily evaluating mental fatigue comprises: an operation unit (4); an imaging unit for measuring ambient light (5); a display screen (2) or a light-emitting element (3) for presenting a flashing image or light while a flicker frequency of the flashing source is being monotonically changed from a start frequency to an ending frequency; and a recording unit for, when a user operates the operation unit (4) as the user perceives a flicker, recording the flicker frequency at the time point as a measured frequency, wherein: a first frequency datum, which is the measured frequency measured when the user is in a healthy condition, is associated with a first luminance datum, which is a measured ambient luminance, and the associated datum is stored in the recording unit, a proportion of decrease of a second frequency datum, which is the measured frequency measured when the user is not in a healthy condition, from the first frequency datum recorded in the recording unit and associated with the first luminance datum which has the same or similar order of magnitude to a second luminance datum, which is a measured ambient luminance, is calculated to evaluate a degree of fatigue of the user.

20 Claims, 3 Drawing Sheets

(a)  (b)

PORTABLE TERMINAL DEVICE HAVING FUNCTION OF MEASURING MENTAL FATIGUE AND ITS MEASURING METHOD

TECHNICAL FIELD

The present invention relates to the measurement of human mental fatigue, particularly to a portable terminal device having a function of measuring mental fatigue and its measuring method.

BACKGROUND ART

In recent years, health hazards and industrial accidents caused by mental fatigue due to overwork have become a social problem.

A flicker test is a known method of measuring mental fatigue. The test relies on human inability to perceive a light pulses, i.e., a flicker, when the light source is flashing at high speeds; however, as the speed (frequency) decreases, perception becomes possible when the frequency is dropped to a certain value. The frequency at which the human perceives the flicker is called a flicker perception threshold, which is known to vary depending on mental fatigue. More specifically, the flicker perception threshold decreases as fatigue becomes more intense; that is, a person cannot perceive a flicker at high frequency when mental fatigue is intense, and perception finally becomes possible when the frequency is dropped to a smaller value than that of a frequency of a flicker that is perceivable by a person in a healthy condition. Using this phenomenon, various flicker test methods and systems were suggested.

For example, Patent Document 1 discloses a system in which a host computer remotely controls a computer terminal in front of the test subject via a network, so as to present some kind of stimulation to the test subject, control the stimulation, and record the reaction of the test subject, thereby measuring the functioning eyesight (actual eyesight) of eyes of the test subject under stress. The document also discloses a method of measurement of flicker perception eyesight to determine the ability to perceive a flicker, as an example of eyesight measurement.

Patent Document 2 discloses a system for reducing the amount of labor necessary for managing the degree of fatigue. The system carries out the presentation and control of flicker stimulation and the measurement of a flicker perception reaction under the control of a computer using a dedicated eyesight-checker containing a light-emitting unit (LED). The degree of fatigue is determined based on the data stored in the computer.

Patent Document 3 discloses a system comprising a flashing light emitting display device and a computer terminal. The flashing light emitting display device presents flicker stimulation under the control of a computer terminal via a communication cable, and the computer terminal records push-button operations as a flicker perception reaction. The measurement data is compared with other data previously stored to estimate the degree of fatigue.

CITATION LIST

[Patent Literature]
[Patent Document 1]
Japanese Unexamined Patent Publication No. 2001-309887

[Patent Document 2]
Japanese Unexamined Patent Publication No. 2001-218756
[Patent Document 3]
Japanese Unexamined Patent Publication No. 2003-70773

SUMMARY OF INVENTION

Technical Problem

The technology of Patent Document 1 is capable of the measurement of eyesight when the eyes are under stress, or the measurement of flicker perception eyesight; however, this technology is incapable of the measurement of human mental fatigue.

Further, in Patent Document 2, the evaluation was performed using statistical data (showing a relationship between perceived flashing frequency and the degree of fatigue based on age), which requires the test subjects to concern themselves with cumbersome registration of their ages. Moreover, the evaluation was performed only in consideration of age and no other individual difference was taken into account. Therefore, the evaluation of mental fatigue is not accurate. Patent Document 3 has the similar deficiencies.

Further, none of Patent Documents 1 to 3 carries out evaluation in consideration of the fact that the flicker perception frequency is influenced by ambient light. Therefore, the evaluation of mental fatigue is not accurate. The influence of ambient light may be eliminated by commanding the test subject to look into the measurement device or to press his/her eyes onto the measurement devices of Patent Documents 1 to 3. However, this forces the user into an uncomfortable posture, increasing the burden of the user.

Furthermore, all of the systems disclosed in Patent Documents 1 to 3 are systems using a computer and/or other dedicated devices, and are not for personal use. Therefore, the systems do not allow the user to easily measure mental fatigue in an unspecified location.

The present invention was made to solve the foregoing problems and aims to provide a portable terminal device having a function of measuring mental fatigue and its measuring method. The portable terminal device of the present invention allows the user to easily measure and evaluate mental fatigue in any location without much difficulty.

Solution to Problem

The inventors of the present invention found that, because the flicker perception threshold of an individual having a general healthy condition is stable, the mental fatigue of an individual after a given brain work time can be quantified by measuring a change in the flicker perception threshold at the target time using the flicker perception threshold in general healthy condition as a standard value. Based on this finding, the inventors completed the present invention wherein the mental fatigue is measured with using a portable terminal device.

Specifically, the portable terminal device according to the present invention is capable of measuring mental fatigue comprising: an operation unit; an imaging unit for measuring ambient light; a display screen for displaying a flashing image while a flicker frequency of the flashing image is being monotonically changed with time from a start frequency to an ending frequency; and a recording unit for, when a user operates the operation unit as the user perceives a flicker during the display of a flashing image, recording the flicker frequency at the time point as a measured frequency, wherein: a first frequency datum, which is the measured frequency measured when the user is specified as healthy via the operation unit, is associated with a first luminance datum, which is the ambient light measured by the imaging unit, and the associated datum is stored in the recording unit, a proportion of decrease of a second frequency datum, which is the measured frequency measured when the user is not specified as healthy via the operation unit, from the first frequency datum associated with the first luminance datum having the same order of magnitude as that of a second luminance datum, which is the ambient light measured by the imaging unit, is calculated to evaluate a degree of fatigue of the user, and the degree of fatigue is displayed on the display screen.

The mobile phone may further include a light-emitting element, and may be structured to present a flashing light of the light-emitting element in stead of presenting a flashing image.

The mobile phone may be arranged so that when the first luminance datum having the same order of magnitude as that of the second luminance datum is not found in the recording unit, a third frequency datum corresponding to the second luminance datum is found by interpolation using a plurality of the first luminance data and the corresponding first frequency data, and a proportion of decrease of the second frequency datum from the third frequency datum is calculated to evaluate the degree of fatigue of the user.

The mobile phone may be arranged so that when the first luminance datum having the same order of magnitude as that of the second luminance datum is not found in the recording unit, a first frequency datum closest to the second luminance datum is determined among a plurality of the first luminance data, a value found by multiplying a logarithmic value of a value, which is found by subtracting the first luminance datum from the second luminance datum, by 1.5 is added to the first frequency datum associated with the determined first luminance datum and recorded in the recording unit so as to find the third frequency datum corresponding to the second luminance datum, and a proportion of decrease of the second frequency datum from the third frequency datum is calculated to evaluate the degree of fatigue of the user.

The mobile phone may be arranged so that a plurality of conditions for flicker presentation, each of which comprises a start frequency, an ending frequency, and a speed of change in flicker frequency, are stored in the recording unit, and the flicker display is carried out using one of the conditions selected at random.

The mobile phone may be arranged so that the first frequency datum is a value obtained by calculating an average of measurement frequencies which differ from each other by 1 Hz or less, among a plurality of the measurement frequencies obtained by performing plural times of measurement of a frequency when the user is specified as healthy via the operation unit.

The method of measuring mental fatigue according to the present invention is performed by a person other than a doctor, using a portable terminal device comprising an operation unit; an imaging unit; a display screen; and a recording unit; the method comprising: a first step in which the imaging unit measures ambient light; a second step in which the display screen displays a flashing image while a flicker frequency of the flashing image is being monotonically changed with time from a start frequency to an ending frequency; a third step in which the recording unit, when a user operates the operation unit as the user perceives a flicker during the display of a flashing image, records the flicker frequency at the time point as a measured frequency; a fourth step in which a first frequency datum, which is the measured frequency measured when the user is specified as healthy via the operation unit, is associated with a first luminance datum, which is the ambient light measured by the imaging unit, and the associated datum is stored in the recording unit, a fifth step in which a proportion of decrease of a second frequency datum, which is the measured frequency measured when the user is not specified as healthy via the operation unit, from the first frequency datum associated with the first luminance datum having the same order of magnitude as that of a second luminance datum, which is the ambient light measured by the imaging unit, is calculated to evaluate a degree of fatigue of the user, and the degree of fatigue is displayed on the display screen.

In the above method, the mobile terminal device may further include a light-emitting element, and may be structured to present a flashing light of the light-emitting element in stead of presenting a flashing image.

The above method may further comprise: a sixth step in which, when the first luminance datum having the same order of magnitude as that of the second luminance datum is not found in the recording unit, a third frequency datum corresponding to the second luminance datum is found by interpolation using a plurality of the first luminance data and the corresponding first frequency data, and a proportion of decrease of the second frequency datum from the third frequency datum is calculated to evaluate the degree of fatigue of the user.

The above method may further comprise: a sixth step in which, when the first luminance datum having the same order of magnitude as that of the second luminance datum is not found in the recording unit, a first frequency datum closest to the second luminance datum is determined among a plurality of the first luminance data, a value found by multiplying a logarithmic value of a value, which is found by subtracting the first luminance datum from the second luminance datum, by 1.5 is added to the first frequency datum associated with the determined first luminance datum and recorded in the recording unit so as to find the third frequency datum corresponding to the second luminance datum, and a proportion of decrease of the second frequency datum from the third frequency datum is calculated to evaluate the degree of fatigue of the user.

The above method may further comprises: a seventh step in which a plurality of conditions for flicker display, each of which comprises a start frequency, an ending frequency, and a speed of change in flicker frequency, are stored in the recording unit, and the flicker presentation is carried out using one of the conditions selected at random.

The above method may be arranged so that the first frequency datum is a value obtained by calculating an average value of measurement frequencies which differ from each other by 1 Hz or less, among a plurality of the measurement frequencies obtained by performing plural times of measurement of a frequency when the user is specified as healthy via the operation unit.

Advantageous Effects of Invention

The present invention enables easy measurement of human fatigue using a basic function of a portable terminal device, such as a mobile phone or PHS, without requiring other external devices.

Further, according to the present invention, the measurement can be performed in an open environment where the user simply observes the flashing image or the flashing light of the light-emitting unit with an about 50 cm interval between the eyes and the portable terminal device; and the user is not forced to look into the measurement device or press his/her eyes onto the measurement device. Therefore, the burden of the user is greatly reduced.

In this method, measurement of ambient light is also carried out at each measurement of human fatigue so as to carry out an evaluation of the degree of fatigue with reference to the data of the user in a general healthy condition measured under the same ambient light. Therefore, the present invention performs measurements with higher accuracy than the conventional method.

When the data measured at the same ambient light is not found in the history of flicker frequency data, the method calculates a standard flicker frequency for the user in a general healthy condition using plural values from the stored history of flicker frequency data. Therefore, it is possible to accurately evaluate the degree fatigue even with a relatively small number of measurements.

Further, the method allows for accumulation of data of continuous measurements of the degree of fatigue for a certain period of time, thereby allowing an individual to maintain high-level health management. More specifically, rapidness/moderateness of the change in the degree of fatigue are an important index to determine human health. Therefore, the presentation of information depending on the change in degree of fatigue is useful for health management. For example, if the change in degree of fatigue is more rapid than a certain degree, it is effective to display a message on a mobile phone screen such that an immediate care is required; or if the degree of fatigue shows periodic extreme amplitude, it is effective to display a message to inform that the user needs some rest and relaxation to ease the amplitude.

Currently, a majority of the population has a mobile phone for personal use. The program of the present invention allows for measurement of fatigue by simply installing the program to a mobile phone. Chronic fatigue is generally very difficult to notice as a subjective symptom. However, because the program allows very easy evaluation based on physiological and objective cognitive reaction, the program improves the management of health-care at the individual level, which further contributes to a decrease in disease rate, a decrease in economic burden on medical cost, or improvement of quality of life.

Figure 1:
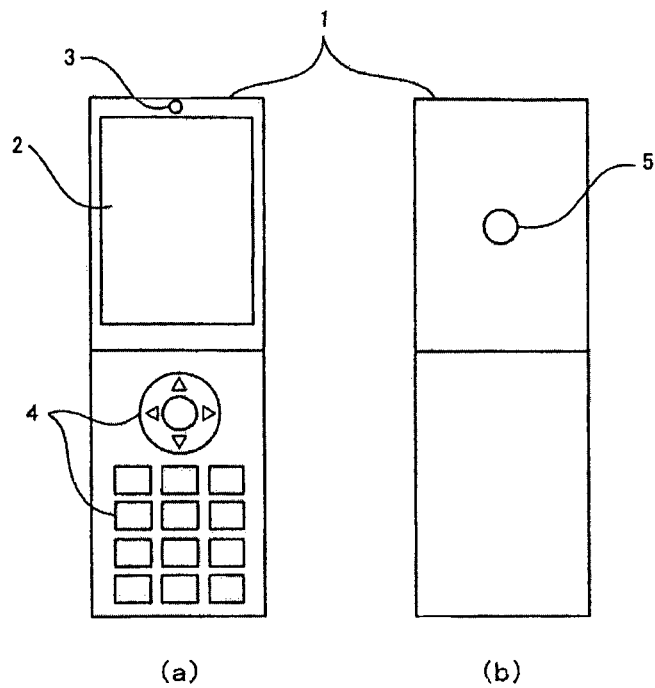
FIG. 1 is an exterior view of a portable terminal device having a function of measuring mental fatigue, according to an embodiment of the present invention.

REFERENCE NUMERALS 1 portable terminal device (mobile phone)
2 liquid crystal screen
3 LED
4 operating means
5 camera lens
11 arithmetic processing unit (CPU)
12 read-only memory (ROM)
13 rewritable memory (RAM)
14 recording unit
15 communication unit
16 display unit
17 LED unit
18 imaging unit
19 clock unit
20 operation unit
21 internal bus

BEST MODE FOR CARRYING OUT THE INVENTION

One embodiment of the present invention is described below with reference to the attached figures. Hereinafter, "fatigue" means mental fatigue, unless otherwise specified.

FIG. 1 is an exterior view of a portable terminal device, which is a mobile phone in this case, having a function of measuring mental fatigue, according to an embodiment of the present invention. FIG. 1(a) is a front view, and FIG. 1(b) is a back view. The mobile phone 1 is a general mobile phone comprising a liquid crystal screen 2, an LED 3, an operating means 4 such as keys or pads, and a camera lens 5. FIG. 1 illustrates componential members involved in the following operation, omitting the other componential members.

Figure 2:
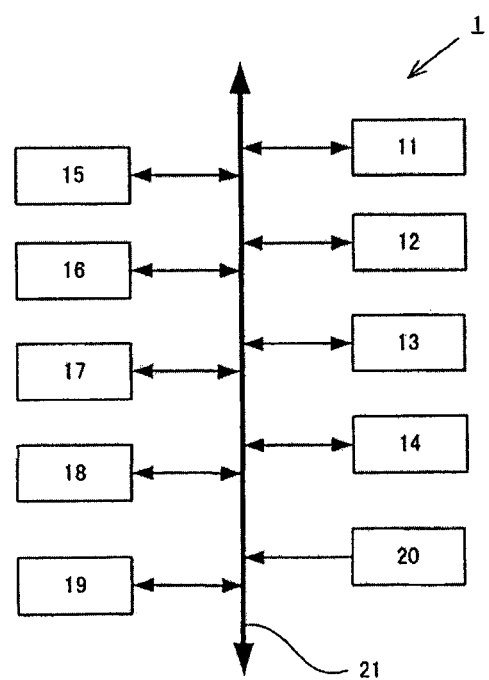
FIG. 2 is a block diagram showing an internal structure of the portable terminal device shown in FIG. 1.

FIG. 2 is a block diagram showing an internal structure of a mobile phone 1. The mobile phone 1 includes an arithmetic processing unit (CPU, hereinafter) 11 for controlling the entire operation of the mobile phone, a nonvolatile read-only memory (ROM, hereinafter) 12 storing a program etc., a volatile rewritable memory (RAM, hereinafter) 13 for temporarily storing data, a nonvolatile rewritable recording unit 14 for continuously storing data, a communication unit 15 for sending/receiving radio waves to/from a mobile phone base station (not shown), a display unit 16, a LED unit 17, an imaging unit 18, a clock unit 19, an operation unit 20, and an internal bus 21 for exchanging data (including control information) between the units. The operation unit 20 includes an operating means 4 such as keys or pads. The display unit 16 includes a liquid crystal screen 2 and a driving unit (not shown) for driving the liquid crystal screen 2. The LED unit 17 includes a LED 3 and a driving unit (not shown) for driving the LED 3. The imaging unit 18 includes an imaging element (not shown) such as a CCD or CMOS sensor, an optical system including a lens 5, and a driving unit (not shown) for driving the lens 5. The clock unit 19 is a means for outputting information of the current time using an internal clock such as a timer.

A mobile phone 1 having a function of measuring mental fatigue according to an embodiment of the present invention presents image or light which periodically changes in luminance, using the liquid crystal screen 2 or a LED 3 shown in FIG. 1 and FIG. 2. When the user perceives a flicker in the flashing image or light, the user operates the operating means 4, so that the degree of fatigue of the user is measured and evaluated.

Figure 3:
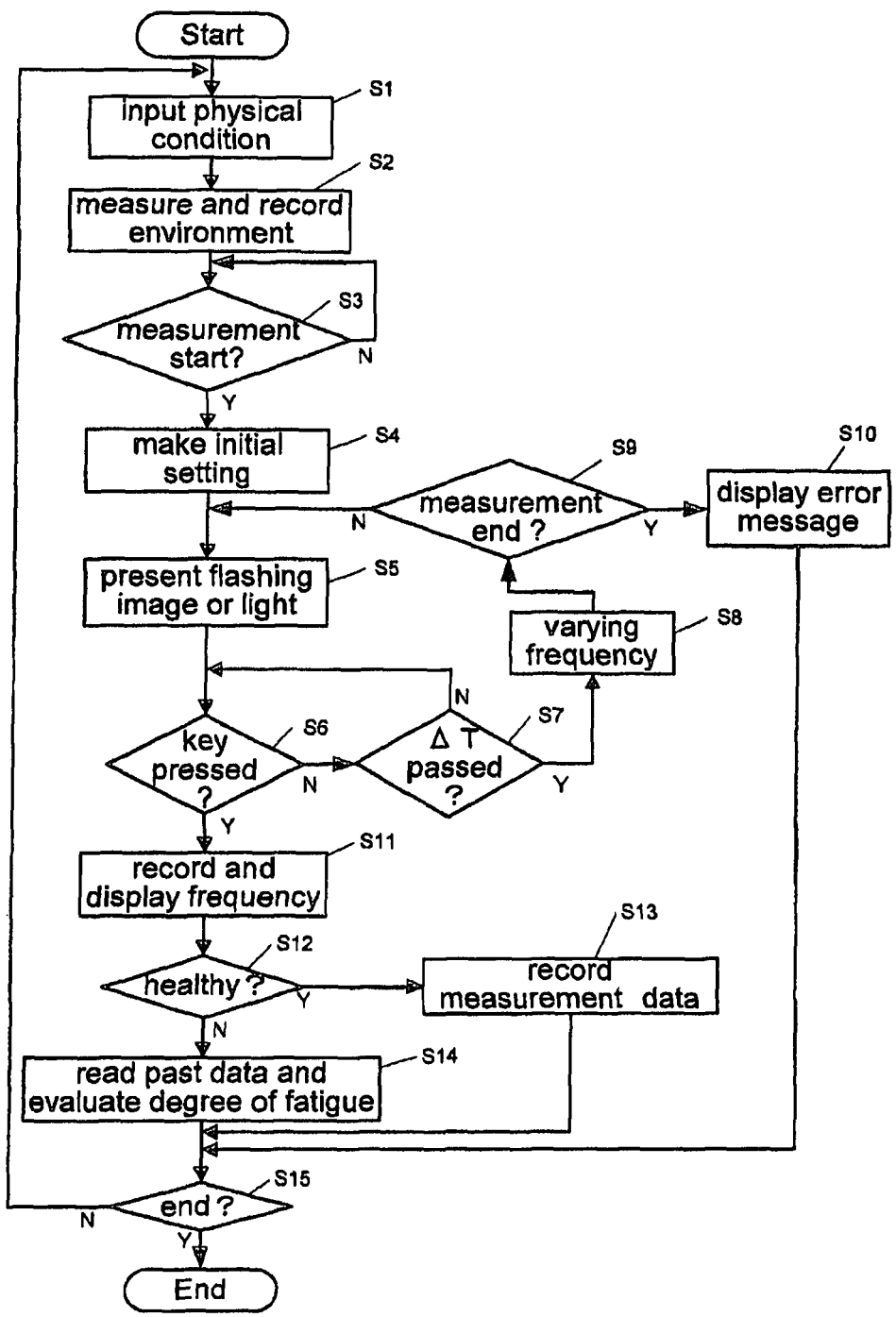
FIG. 3 is a flow chart showing operation of the portable terminal device according to an embodiment of the present invention.

The following describes the details of the measurement and evaluation of mental fatigue according to the present embodiment. FIG. 3 is a flow chart showing operation of a mobile phone 1 of the present embodiment. In the following description, all operations are explained as being carried out by a CPU, unless otherwise specified. The CPU 11 reads out necessary data as required from the ROM 12 and the recording unit 14, processes the data using a predetermined area of the RAM 13 as work area, and stores the temporary results and the final processing results in the recording unit 14 if necessary. It is also assumed that the initial condition required for the measurement is previously stored in the recording unit 14.

First, the liquid crystal screen 2 displays a menu that demands the user to decide whether or not to carry out fatigue measurement. When the user operates the operating means 4 to carry out fatigue measurement, the following fatigue measurement is started.

In Step S1, the user is asked to provide information about the current body condition. For example, the liquid crystal screen 2 displays a question as to whether the user has a healthy body condition or not, and the operation is suspended until the user provides the information. In response to the user's input through the operating means 4, the CPU 11 acquires data corresponding to the user's input of the current body condition, and associates the data with the current time (including day, month, and year) obtained from the clock unit 19 before storing the data in the RAM 13.

In Step S2, ambient light (light quantity) is measured, and the measurement result is stored in the RAM 13. For example, the imaging unit 18 is driven to carry out image-taking without using flash under a predetermined shooting condition (including shutter time, focus etc.). This allows the CPU 11 to acquire a signal corresponding to the light quantity received from each pixel of the imaging element. The obtained light quantities are evened off to find an average light quantity per pixel, which is stored in the RAM 13 as luminance data. Insofar as the information regarding ambient light is obtained and a representative data is found from the measured values, statistics other than the average value, such as summation, median, mode, etc., may also be used.

In Step S3, the sequence is suspended until the measurement start command is inputted. In response to the measurement start command, the sequence goes to Step S4.

In Step S4, the initial condition for the measurement is set. More specifically, a start frequency fs, an end frequency fe, a frequency difference $\Delta f$, and a time difference $\Delta T$ are read out from the recording unit 14. The start frequency fs is set to a flicker frequency f. For example, the condition is set so that fs=60 (Hz), fe=30 (Hz), $\Delta f$=1.0 (Hz), and $\Delta T$=1 (seconds). Further, the current time is acquired from the clock unit 19 and set to the time parameter T, so as to change the flicker frequency f by the frequency difference $\Delta f$ using the time difference $\Delta T$ (described later).

The following describes operation where fs>fe. As described later, this condition corresponds to a change of the flicker frequency f from a high value to a low value; more specifically, a change from a state where the user cannot perceive the flashing light source as a flicker to a state where the user can perceive the flicker after a certain time has elapsed.

In Step S5, a flashing image or light is presented at the current frequency f=fs determined in Step S4. Incidentally, before or after the flashing presentation, an instruction screen regarding operations with the operating means 4 may be presented to the user. The flashing presentation can be performed using a liquid crystal screen 2 or a LED 3.

Figure 4:
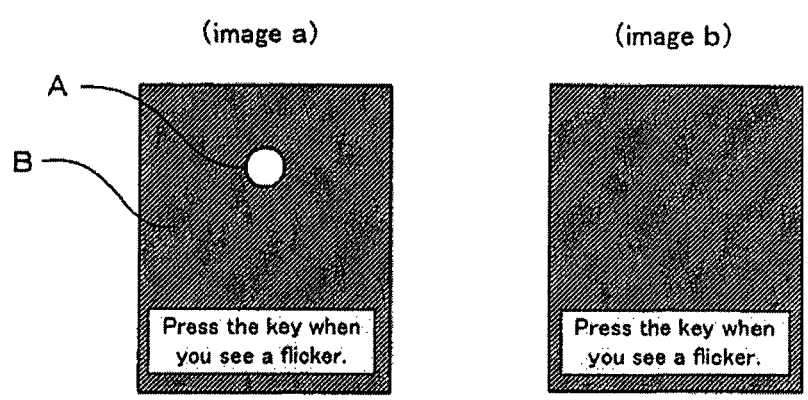
FIG. 4 is a drawing showing an example of flashing image displayed on a liquid crystal screen.

For example, in the case of using the liquid crystal screen 2, a plurality of still images functioning as the flashing light source are previously stored in the recording unit 20. FIG. 4 illustrates an example of two images used as a flashing light source. An image a has the same size (pixels) as that of the liquid crystal screen 2. In the image a, a small region A of a predetermined size having a high-luminance is provided in the vicinity of the center, surrounded by a periphery B having a low, uniform luminance. An image b has the same size (pixels) as that of the liquid crystal screen, and has a low, uniform luminance as with the periphery B of the image a. For example, the luminance of the region A is a maximum luminance displayable in the mobile phone 1, and the luminance of the periphery B is a minimum luminance displayable in the mobile phone 1. More specifically, the region A is a circular region with 100 cd (Candela)/m$^2$ in luminance, and about 5 mm in diameter (corresponding to a viewing angle of 0.5 to 0.6° when the mobile phone 1 is about 50 cm distant).

The CPU 11 reads out the image a and the image b shown in FIG. 4 into the RAM 13, and alternately transmits these two images to the display unit 16 at predetermined time intervals. The driving unit of the display unit 16 displays the transmitted image data on the liquid crystal screen 2. Here, the CPU 11 calculates the time $\Delta t$ for displaying each image from the flicker frequency f according to $\Delta t=1/(2\times f)$, repeatedly acquires the current time information from the clock unit 19, and alternately carries out the operation of maintaining the display of either the image a or b until $\Delta t$ has elapsed, and the operation of switching the display to the other image after the $\Delta t$ has elapsed. With this sequence of operations, the flashing image of the circle A is displayed to the user at the flicker frequency f. Nevertheless, a text message that reads "please press the key when the image starts flickering" in the image a or b is not flashing and is shown still in the same position.

In the case of using the LED 3, the CPU 11 transmits the flicker frequency f to the driving unit of the LED unit 17 at a predetermined timing. In response to this, the driving unit applies a predetermined voltage which changes at the flicker frequency f to the LED 3, thereby flashing the LED 3. Examples of the voltage to be applied to the LED 3 include a sine wave (cosine wave) and a rectangular wave having a duty of 50%. In this case, for example, a text message that reads "please press the key when the light starts flickering", may be displayed on the liquid crystal screen 2 before the LED starts flashing or during the flashing.

The threshold is determined by either using the frequency at which the user perceives the flicker in the phase of transition from a high speed flashing to a low speed flashing, or a frequency at which the flicker becomes invisible in the phase of reverse transition (low speed flashing to high speed flashing). However, because the frequency at which the user starts perceiving the flicker is a lower value and relatively stable, the present method adopts a frequency at which the user starts perceiving the flicker.

It is desirable to keep the same measuring condition as much as possible, except for that of ambient light. For example, the liquid crystal screen 2 may display a message to instruct the user to look at the flashing image or LED from the front at a distance of about 50 cm from the eyes by simply stretching out his/her arm.

In Step S6, a judgment is carried out as to whether the operating means 4 (keys or the like) have been operated by the user. In Step S5, the liquid crystal screen displays a message "please press a key when the light starts flickering" or the like. If the user presses a key as the user perceives the flicker of the circle A displayed on the liquid crystal screen or the flicker of the LED, the sequence goes to Step S11. If the key is not pressed yet, the sequence goes to Step S7.

In Step S7, the current time t is acquired from the clock unit 19 to be compared with the time parameter T. If the difference (t−T) is smaller than the time difference $\Delta T$ (t−T<$\Delta T$), the sequence goes back to Step S6. If the difference (t−T) is greater than or equal to the time difference $\Delta T$ (t−T$\geq\Delta T$), the sequence goes to Step S8.

In Step S8, the frequency difference $\Delta f$ is subtracted from the current flicker frequency f to determine a new flicker frequency f (f=f−$\Delta f$). After the current time t is set to the time parameter T obtained in Step S7, the sequence goes to Step S9.

In Step S9, a judgment is carried out to determine whether the flicker frequency f exceeds an ending frequency fe. If the judgment concludes as f$\geq$fe, the sequence goes back to Step S5 so that the flicker is given at a new flicker frequency f. If the judgment concludes as f<fe, the sequence goes to Step S10 to carry out an error display, and then goes to Step S15. When the key is not pressed by the user while the flicker is on, the sequence goes to Step S10.

In Step S11, the flicker (or flashing) presentation is stopped, and the value of the current flicker frequency f is displayed on the screen, the current time (including date, month, and year) is acquired from the clock unit 19, and the current time and the flicker frequency f are associated with each other and are stored in the RAM 13.

In Steps S5 to S9, the flicker presentation is carried out while adjusting the flicker frequency f according to the frequency difference Δf. The adjustment is performed every time the time ΔT, from the start frequency fs to the ending frequency fe, is elapsed. Accordingly, it is possible to obtain a flicker frequency upon the key pressing operation by the user.

In Step S12, the sequence is divided into two operations depending on the data of the body condition stored in the RAM 13 in Step S1. More specifically, if the user has selected that he has a healthy condition in Step S1, the sequence moves to Step S13, and the ambient light data found in Step S2 is associated with the flicker frequency f and the current time stored in the RAM 13 in Step S11. The associated data is stored in the recording unit 14. If the user has not selected that he has the healthy condition in Step S1, the sequence goes to Step S14.

In Step S14, a search is carried out to find a flicker frequency corresponding to the ambient light data of a similar degree from the history of measurement results stored in the recording unit 14. Using the flicker frequency as a reference value, the proportion of decrease of the current frequency from the reference value is calculated to evaluate the degree of fatigue of the user, and the evaluation result is displayed on the liquid crystal screen 2. For this operation, it is necessary that the recording unit 14 stores a certain number of history data. If there is no data in the recording unit 14, or the amount is less than required, the liquid crystal screen 2 displays a message that the measurement (evaluation) is not possible.

The "ambient light data of a similar degree" denotes ambient light data of the same order of magnitude (having a same most significant digit). The frequency of the threshold at which the flicker is perceived is considered to logarithmically change with respect to the ambient light (luminance). For example, if the ambient luminance is changed from 100 $cd/m^2$ to 10 $cd/m^2$, the frequency of the threshold is assumed to decrease by 1 to 2 Hz. Further, if the luminance of the light-emitting unit is 1000 $cd/m^2$, and the ambient light is less than 1000 $cd/m^2$, the threshold (Hz) decreases by a value of 1.5 times of the logarithmic value of the decrease in luminance. If the ambient light is more than 1000 $cd/m^2$, the threshold (Hz) decreases by a value of three times of the logarithmic value of the decrease in luminance.

Since the threshold frequency measured when the user is in a healthy condition varies depending on the individual difference and age, the evaluation of the degree of fatigue of the user is performed based on the proportion of the decrease from the reference value (percentage on the reference value). For example, a proportion of decrease of 3 to 5% from the reference value is evaluated as "moderate", a proportion of decrease of 5 to 7.5% from the reference value is evaluated as "intermediate", a proportion of decrease of 7.5 to 10% from the reference value is evaluated as "severe", and a proportion of decrease of 10% or greater is evaluated as "hazardous".

When the ambient light data close to the current measurement data is not found even though a certain amount of data history is stored in the recording unit 14, interpolation or extrapolation is carried out using plural items of ambient light data stored in the recording unit 14 to calculate a frequency corresponding to the currently measured luminance data. The resulting frequency is used as a reference value for the evaluation of degree of fatigue. Accordingly, the evaluation requires history data in an amount sufficient for carrying out the interpolation or extrapolation of the data to enable calculation of the luminance data.

When the ambient light data close to the luminance data (B0) measured in Step S2 is not found in the recording unit 14, an alternative calculation is carried out to determine the closest luminance data (B1) in the recording unit 14 with an assumption that an increase of luminance by an order of magnitude increases the threshold by 1.5 Hz (conversely, a decrease of luminance by an order of magnitude decreases the threshold by 1.5 Hz). The flicker frequency (f1) corresponding to the luminance data thus found is read out from the recording unit 14 and is added to a value determined by multiplying the logarithmic value (log(B1−B0)) of the luminance data difference (B1−B0) by 1.5 (Hz), thereby taking the calculated value (f1+1.5×log (B1−B0)) as the reference value.

Note that, as mentioned above, depending on the luminance of the light-emitting unit and the luminance of ambient light, it is preferable in some cases to find the reference value by multiplying the logarithmic value by 3 Hz instead of 1.5 Hz.

When the amount of data in healthy condition used for the evaluation is less than required, a default value may be used. Though it depends on the device and the experimenter, there are many reports of measurements using a threshold frequency of 42 Hz. When the evaluation is carried out using this value as a reference value, the degree of fatigue based on a change in threshold frequency is determined as follows. A decrease of 1.5 Hz to 2 Hz from the reference value is evaluated as "moderate", a decrease of 2 Hz to 3 Hz from the reference value is evaluated as "intermediate", a decrease of 3 Hz to 4 Hz from the reference value is evaluated as "severe", and a decrease of 4 Hz or greater is evaluated as "hazardous".

Finally, in Step S15, a judgment is carried out to determine whether the instruction of termination is given. If the instruction is not given, the sequence goes back to Step S1. The above described operations are repeated until the instruction of termination is given.

With the above series of operations, the user can easily measure his/her degree of fatigue at any time and in any place.

The detailed description of the above embodiment is not to limit the present invention. More specifically, the present invention is not limited to the description of the embodiments above, but may be altered by, for example, making various modifications to the flow chart in FIG. 3.

In the above description of Step S5 to S10 in FIG. 3, the flicker frequency is linearly decreased; however, the present invention is not limited to this method. For example, the flicker frequency may be increased from a low frequency. Further, insofar as the change is monotonic, the frequency may be increased/decreased nonlinearly. When the flicker frequency is monotonically increased, the start frequency is set smaller than the ending frequency (fs<fe), and the start frequency is set to a value at which the user perceives the flicker. The liquid crystal screen may display an instruction such as operating a key when the flicker becomes unperceivable.

Instead of using only one kind of initial condition, i.e., one kind of the set of start frequency fs, ending frequency fe, frequency difference Δf, and time difference ΔT, it is possible to previously store plural different initial conditions in the recording unit 14, and reads out one of them at random in Step S4 of setting the initial condition. With this variation, the user cannot predict the timing of the perception of the flicker from the beginning of the measurement even when the user performs the test frequently. As a result, the accuracy of the measurement result increases. By varying at least one value among the four parameters (fs, fe, $\Delta f$, $\Delta T$) of the initial conditions, the prediction of the timing becomes difficult. For example, under the condition where fs=60 (Hz), fe=30 (Hz), and $\Delta T$=1 (seconds), the $\Delta f$ can be varied among 1.2, 1.0 and 0.8 Hz.

The threshold may also be determined by repeating Steps S4 to S13 for 3 to 5 times, selecting measurements with a difference of 1 Hz or less, and finding an average of the measurements.

The device used for the measurement is not limited to mobile phones. Examples of the devices include portable terminal devices such as a PHS (Personal Handyphone System) and a PDA (Personal Digital Assistant). Further, the display screen is not limited to liquid crystal screens. For example a mobile phone having a kind of display screen other than liquid crystal, such as an EL display (Electroluminescence Display) may be used. Further, instead of a mobile phone containing an LED, it is possible to use a light-emitting element capable of emitting visible light and flashing the light at a predetermined frequency.

Further, though the above embodiment uses two images as the images displayed on the liquid crystal screen, the present invention is not limited to this structure, and three or more images may be used. For example, an image c, which has an intermediate luminance of the images a and b in FIG. 4, may be used so that the screen repeatedly displays images in the order of image a→image c→image b→image a. For example, the image c is created by finding an average of the corresponding pixel data of the image a and the image b. In this case, in Step S5, the time for displaying each image is determined using the flicker frequency f according to $\Delta t=1/(3\times f)$. When a plurality of images is used, the time for displaying each image is appropriately set depending on the luminance of the image being used. Moreover, instead of using an image in which a part of the pixels of the image has a different luminance from those of the rest of the pixels, it is also possible to use plural images that each have a different uniform luminance.

Further, instead of preparing images to be displayed in advance, it is possible to cause the CPU 11 to generate images and store them in the RAM 13 before the measurement, and carry out the flicker display using the images.

Though the above embodiment is structured so that the program for measuring the degree of mental fatigue is previously stored in the ROM 12, it is also possible to download the program to the mobile phone by accessing an Internet server, or installing the program in the mobile phone via a detachable recording medium, such as a memory card.

Though the above embodiment is structured so that the recording unit stores only the result of the measurement in which the user determines that the user is in healthy condition, it is also possible to store the result of the measurement in which the user determines that the user is not in healthy condition. In this case, the perceived flicker frequency, the current time (including day, month, and year), the ambient light data, and the evaluation results of the degree of fatigue are associated with each other in the recording unit. Further, it is possible to transmit data from the recording unit 14 to a computer server or the like at certain time intervals or in response to the user's instruction, thereby storing data for a long period as a database. Storage to the database may be performed via a detachable recording medium, such as a memory card. As such, the degree of fatigue can be continuously measured and evaluated at a certain period of time, and the measurement and the evaluation data can be accumulated. This enables high-level of health management for individuals. For example, when the degree of fatigue shows a rapid change beyond a certain level (for example, the measured frequency is decreased by 7.5% or more within a period from three days to a week), a message that urgent care is required is displayed on the screen of the mobile phone. Further, when the degree of fatigue periodically reaches an extreme amplitude (for example, the measured frequency is decreased or increased by 7.5% or more from the reference frequency within a period from three days to a week), a message that some rest and relaxation is required to reduce the amplitude is displayed on the screen of the mobile phone. Whether the change in the degree of fatigue is sharp or moderate is an important index for the determination of human health; therefore, a presentation of information according to the change in the degree of fatigue is very useful for individual health management.

It is also possible to determine the user's health condition based on a combination of the flicker measurement results accumulated over a certain period of time and other physiological indices. Examples of the information to be combined with the flicker measurement results include blood pressure, blood screening data (blood screening data given by a medical institution), age, occupation, and working condition. In the case the user uses his/her mobile phone to access to the server, the server may carry out an evaluation of the health condition of the user in response to the access, transmitting the evaluation results to the mobile phone of the user, having them displayed on the screen of the mobile phone.

INDUSTRIAL APPLICABILITY

The present invention enables easy measurement of human fatigue by using only the basic functions of a portable terminal device, such as a mobile phone or PHS, without requiring other external devices.

The invention claimed is:

1. A portable terminal device capable of measuring mental fatigue comprising:

an operation unit;

an imaging unit for measuring ambient light;

a display screen for displaying a flashing image while a flicker frequency of the flashing image is being monotonically changed with time from a start frequency to an ending frequency; and a recording unit for, when a user operates the operation unit as the user perceives a flicker during the display of a flashing image, recording the flicker frequency at the time point as a measured frequency, wherein:

a first frequency datum, which is the measured frequency measured when the user is specified as healthy via the operation unit, is associated with a first luminance datum, which is the ambient light measured by the imaging unit, and the associated datum is stored in the recording unit, a proportion of decrease of a second frequency datum, which is the measured frequency measured when the user is not specified as healthy via the operation unit, from the first frequency datum associated with the first luminance datum having the same order of magnitude as that of a second luminance datum, which is the ambient light measured by the imaging unit, is calculated to evaluate a degree of fatigue of the user, and the degree of fatigue is displayed on the display screen.

2. A portable terminal device capable of measuring mental fatigue comprising:

an operation unit;

an imaging unit for measuring ambient light;

a display screen;

a light-emitting element for presenting a flashing light while a flicker frequency of the flashing light is being monotonically changed with time from a start frequency to an ending frequency; and a recording unit for, when a user operates the operation unit as the user perceives a flicker during the presentation of a flashing light, recording the flicker frequency at the time point as a measured frequency, wherein:

a first frequency datum, which is the measured frequency measured when the user is specified as healthy via the operation unit, is associated with a first luminance datum, which is the ambient light measured by the imaging unit, and the associated datum is stored in the recording unit, a proportion of decrease of a second frequency datum, which is the measured frequency measured when the user is not specified as healthy via the operation unit, from the first frequency datum associated with the first luminance datum having the same order of magnitude as that of a second luminance datum, which is the ambient light measured by the imaging unit, is calculated to evaluate a degree of fatigue of the user, and the degree of fatigue is displayed on the display screen.

3. The portable terminal device capable of measuring mental fatigue according to claim 1, wherein:

when the first luminance datum having the same order of magnitude as that of the second luminance datum is not found in the recording unit, a third frequency datum corresponding to the second luminance datum is found by interpolation using a plurality of the first luminance data and the corresponding first frequency data, and a proportion of decrease of the second frequency datum from the third frequency datum is calculated to evaluate the degree of fatigue of the user.

4. The portable terminal device capable of measuring mental fatigue according to claim 1, wherein:

when the first luminance datum having the same order of magnitude as that of the second luminance datum is not found in the recording unit, a first frequency datum closest to the second luminance datum is determined among a plurality of the first luminance data, a value found by multiplying a logarithmic value of a value, which is found by subtracting the first luminance datum from the second luminance datum, by 1.5 is added to the first frequency datum associated with the determined first luminance datum and recorded in the recording unit so as to find the third frequency datum corresponding to the second luminance datum, and a proportion of decrease of the second frequency datum from the third frequency datum is calculated to evaluate the degree of fatigue of the user.

5. The portable terminal device capable of measuring mental fatigue according to claim 1, wherein:

a plurality of conditions for flicker display, each of which comprises a start frequency, an ending frequency, and a speed of change in flicker frequency, are stored in the recording unit, and the flicker display is carried out using one of the conditions selected at random.

6. The portable terminal device capable of measuring mental fatigue according to claim 1, wherein:

the first frequency datum is a value obtained by calculating an average of measurement frequencies which differ from each other by 1 Hz or less, among a plurality of the measurement frequencies obtained by performing plural times of measurement of a frequency when the user is specified as healthy via the operation unit.

7. The portable terminal device capable of measuring mental fatigue according to claim 2, wherein:

when the first luminance datum having the same order of magnitude as that of the second luminance datum is not found in the recording unit, a third frequency datum corresponding to the second luminance datum is found by interpolation using a plurality of the first luminance data and the corresponding first frequency data, and a proportion of decrease of the second frequency datum from the third frequency datum is calculated to evaluate the degree of fatigue of the user.

8. The portable terminal device capable of measuring mental fatigue according to claim 2, wherein:

when the first luminance datum having the same order of magnitude as that of the second luminance datum is not found in the recording unit, a first frequency datum closest to the second luminance datum is determined among a plurality of the first luminance data, a value found by multiplying a logarithmic value of a value, which is found by subtracting the first luminance datum from the second luminance datum, by 1.5 is added to the first frequency datum associated with the determined first luminance datum and recorded in the recording unit so as to find the third frequency datum corresponding to the second luminance datum, and a proportion of decrease of the second frequency datum from the third frequency datum is calculated to evaluate the degree of fatigue of the user.

9. The portable terminal device capable of measuring mental fatigue according to claim 2, wherein:

a plurality of conditions in flicker presentation, each of which comprises a start frequency, an ending frequency, and a speed of change in flicker frequency are stored in the recording unit, and the flicker presentation is carried out using one of the conditions selected at random.

10. The portable terminal device capable of measuring mental fatigue according to claim 2, wherein:

the first frequency datum is a value obtained by calculating an average of measurement frequencies which differ from each other by 1 Hz or less, among a plurality of the measurement frequencies obtained by performing plural times of measurement of a frequency when the user is specified as healthy via the operation unit.

11. A method of measuring mental fatigue, performed by a person other than a doctor, using a portable terminal device comprising an operation unit; an imaging unit; a display screen; and a recording unit;

the method comprising:
a first step in which the imaging unit measures ambient light;
a second step in which the display screen displays a flashing image while a flicker frequency of the flashing image is being monotonically changed with time from a start frequency to an ending frequency;
a third step in which the recording unit, when a user operates the operation unit as the user perceives a flicker during the display of a flashing image, records the flicker frequency at the time point as a measured frequency;
a fourth step in which a first frequency datum, which is the measured frequency measured when the user is specified as healthy via the operation unit, is associated with a first luminance datum, which is the ambient light measured by the imaging unit, and the associated datum is stored in the recording unit,
a fifth step in which a proportion of decrease of a second frequency datum, which is the measured frequency measured when the user is not specified as healthy via the operation unit, from the first frequency datum associated with the first luminance datum having the same order of magnitude as that of a second luminance datum, which is the ambient light measured by the imaging unit, is calculated to evaluate a degree of fatigue of the user, and the degree of fatigue is displayed on the display screen.

12. A method of measuring mental fatigue, performed by a person other than a doctor, using a portable terminal device comprising an operation unit; an imaging unit; a display screen; a light-emitting element; and a recording unit;

the method comprising:
a first step in which the imaging unit measures ambient light;
a second step in which the light-emitting element presents a flashing light while a flicker frequency of the flashing light is being monotonically changed with time from a start frequency to an ending frequency;
a third step in which the recording unit, when a user operates the operation unit as the user perceives a flicker during the presentation of a flashing light, records the flicker frequency at the time point as a measured frequency;
a fourth step in which a first frequency datum, which is the measured frequency measured when the user is specified as healthy via the operation unit, is associated with a first luminance datum, which is the ambient light measured by the imaging unit, and the associated datum is stored in the recording unit,
a fifth step in which a proportion of decrease of a second frequency datum, which is the measured frequency measured when the user is not specified as healthy via the operation unit, from the first frequency datum associated with the first luminance datum having the same order of magnitude as that of a second luminance datum, which is the ambient light measured by the imaging unit, is calculated to evaluate a degree of fatigue of the user, and the degree of fatigue is displayed on the display screen.

13. The method of measuring mental fatigue according to claim 11, further comprising:
a sixth step in which, when the first luminance datum having the same order of magnitude as that of the second luminance datum is not found in the recording unit, a third frequency datum corresponding to the second luminance datum is found by interpolation using a plurality of the first luminance data and the corresponding first frequency data, and a proportion of decrease of the second frequency datum from the third frequency datum is calculated to evaluate the degree of fatigue of the user.

14. The method of measuring mental fatigue according to claim 11, further comprising:
a sixth step in which, when the first luminance datum having the same order of magnitude as that of the second luminance datum is not found in the recording unit, a first frequency datum closest to the second luminance datum is determined among a plurality of the first luminance data, a value found by multiplying a logarithmic value of a value, which is found by subtracting the first luminance datum from the second luminance datum, by 1.5 is added to the first frequency datum associated with the determined first luminance datum and recorded in the recording unit so as to find the third frequency datum corresponding to the second luminance datum, and a proportion of decrease of the second frequency datum from the third frequency datum is calculated to evaluate the degree of fatigue of the user.

15. The method of measuring mental fatigue according to claim 11, further comprising:
a seventh step in which a plurality of conditions for flicker display, each of which comprises a start frequency, an ending frequency, and a speed of change in flicker frequency, are stored in the recording unit, and the flicker display is carried out using one of the conditions selected at random.

16. The method of measuring mental fatigue according to claim 11, wherein:
the first frequency datum is a value obtained by calculating an average value of measurement frequencies which differ from each other by 1 Hz or less, among a plurality of the measurement frequencies obtained by performing plural times of measurement of a frequency when the user is specified as healthy via the operation unit.

17. The method of measuring mental fatigue according to claim 12, further comprising:
a sixth step in which, when the first luminance datum having the same order of magnitude as that of the second luminance datum is not found in the recording unit, a third frequency datum corresponding to the second luminance datum is found by interpolation using a plurality of the first luminance data and the corresponding first frequency data, and a proportion of decrease of the second frequency datum from the third frequency datum is calculated to evaluate the degree of fatigue of the user.

18. The method of measuring mental fatigue according to claim 12, further comprising:
a sixth step in which, when the first luminance datum having the same order of magnitude as that of the second luminance datum is not found in the recording unit, a first frequency datum closest to the second luminance datum is determined among a plurality of the first luminance data, a value found by multiplying a logarithmic value of a value, which is found by subtracting the first luminance datum from the second luminance datum, by 1.5 is added to the first frequency datum associated with the determined first luminance datum and recorded in the recording unit so as to find the third frequency datum corresponding to the second luminance datum, and a proportion of decrease of the second frequency datum from the third frequency datum is calculated to evaluate the degree of fatigue of the user.

19. The method of measuring mental fatigue according to claim 12, further comprising:

a seventh step in which a plurality of conditions in flicker presentation, each of which comprises a start frequency, an ending frequency, and a speed of change in flicker frequency, are stored in the recording unit, and the flicker presentation is carried out using one of the conditions selected at random.

20. The method of measuring mental fatigue according to claim 12, wherein:

the first frequency datum is a value obtained by calculating an average value of measurement frequencies which differ from each other by 1 Hz or less, among a plurality of the measurement frequencies obtained by performing plural times of measurement of a frequency when the user is specified as healthy via the operation unit.

* * * * *